United States Patent [19]

Komai et al.

[11] Patent Number: 5,018,173

[45] Date of Patent: May 21, 1991

[54] DIAGNOSIS APPARATUS USING X-RAY CT DEVICE

[75] Inventors: Norihiko Komai; Takashi Nishiguchi; Junji Hirayama; Tomoaki Terada, all of Wakayama, Japan

[73] Assignee: Kabushiki Kaisha Toshiba, Kawasaki, Japan

[21] Appl. No.: 421,528

[22] Filed: Oct. 13, 1989

[30] Foreign Application Priority Data

Oct. 18, 1988 [JP] Japan ................... 63-261987

[51] Int. Cl.$^5$ ............... H04N 5/32; G01N 23/00; H05G 1/64; G21K 1/12
[52] U.S. Cl. ........................... 378/4; 378/21; 378/98; 378/99; 358/111
[58] Field of Search ............ 378/4, 98, 53, 21, 99, 378/162; 358/111

[56] References Cited

U.S. PATENT DOCUMENTS

| 4,611,341 | 9/1986 | Brody ........................ 358/111 |
| 4,633,307 | 12/1986 | Honda ....................... 358/111 |
| 4,639,867 | 1/1987 | Suzuki et al. ............... 358/111 |
| 4,706,268 | 11/1987 | Onodera ..................... 358/111 |

FOREIGN PATENT DOCUMENTS 0182200 5/1986 European Pat. Off. .

OTHER PUBLICATIONS

Patent Abstracts of Japan, vol. 9, No. 54 (P-340)(1777), 8 Mar. 1985 & JP-A-59 190 682 (Toshiba K. K. 29.10.1984).

IEEE Transactions on Medical Imaging, vol. MI-4, No. 2, Jun. 1985, pp. 104–113, New York; M. Froeder et al.: "Dynamic Studies of Brain Tumors by the Use of Digital Fluoroscopy", p. 107, lines 26–51.

"Simplified, Noninvasive PEP Measurement of Blood--Barrier Permeability", Journal of Computer Assisted Tomography, vol. 11, No. 3 (May/Jun. 1987), pp. 390–397.

Primary Examiner—Carolyn E. Fields
Assistant Examiner—Don Wong
Attorney, Agent, or Firm—Finnegan, Henderson, Farabow, Garrett and Dunner

[57] ABSTRACT

A diagnosis apparatus using an X-ray CT includes an X-ray scanner for repeatedly scanning a single portion of a subject using an X-ray a plurality of times to output X-ray projection data, an injector for injecting a contrast medium into the subject, a data collecting device for collecting the X-ray projection data output from the X-ray scanner, an image reconstruction device for reconstructing the collected data to generate reconstructed image data, an image analyzing device for analyzing the image data obtained by the image reconstruction device to calculate parameters each representing a state of permeability of blood vessels, a computer for combining the parameters to form diagnosis images, and a display for displaying the diagnosis image.

5 Claims, 5 Drawing Sheets

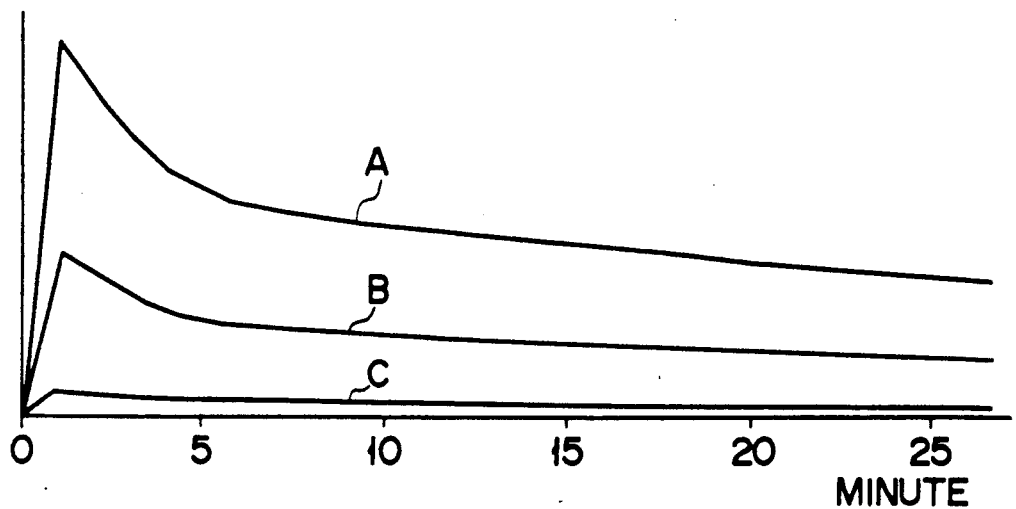
F I G. 5
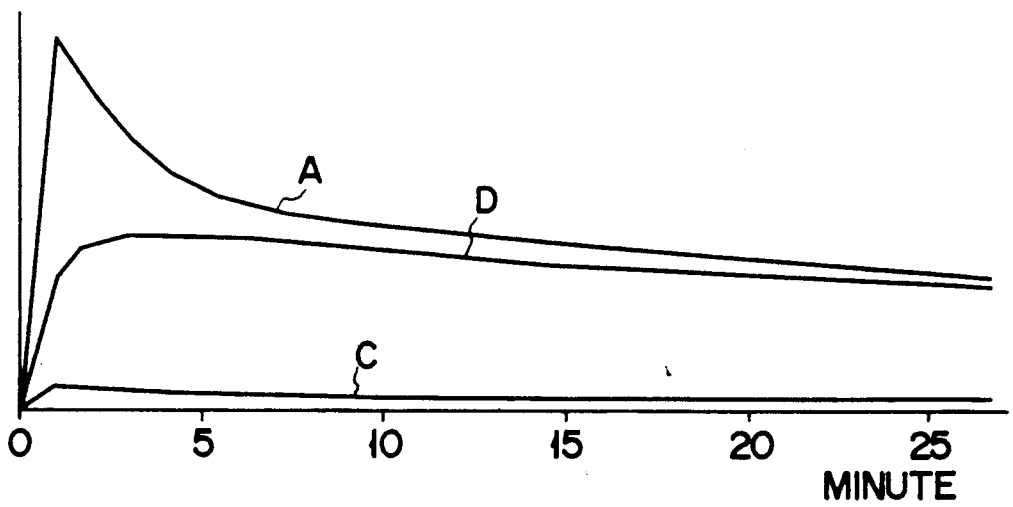
F I G. 6

DIAGNOSIS APPARATUS USING X-RAY CT DEVICE

BACKGROUND OF THE INVENTION

1. Field of the Invention

The present invention relates to a diagnosis apparatus using XCT (X-ray computed tomography) and, more particularly, to a diagnosis apparatus for diagnosing a function of blood vessels by XCT.

2. Description of the Related Art

A demand has arisen for diagnosing a function of blood vessels, in particular, a function of blood vessels in a brain. The blood vessels in a brain has a function called blood brain barriers, and prevent plasm in blood from directly permeating into the brain. However, the blood brain barrier may not function for some reasons, and plasm in the blood may directly permeate in the brain. In order to diagnose such a state, an apparatus for diagnosing a blood brain barrier (BBB) has been developed. Such an apparatus is disclosed in "Simplified, Noninvasive PEP Measurement of Blood-Barrier Permeability", "J comput Assist Tomogr, Vol. 11, No. 3, 1987", pp. 390–397. According to the apparatus in this paper, a radioactive material such as (68G) EDTA is used as a contrast medium, and a subject to which this contrast medium has been injected is scanned by a PET (Position Emission Tomography) device. Parameters associated with a function of a blood brain barrier are calculated in accordance with PET (positron emission tomography) data obtained by this scanning operation, and the parameters are monitored as functional images, and are used for diagnosis.

In the above-mentioned conventional apparatus, a radioactive material is used as a contrast medium. The life of the radioactive material is short and, at most, about several hours. For this reason, the radioactive material serving as a contrast medium must be manufactured immediately before diagnosis. Therefore, an equipment (hot-labo) for manufacturing the contrast medium must be arranged in a diagnosis section. The PET device is used as a scanner to obtain PET data. However, this PET is a very expensive equipment, and has a problem that its space resolution is relatively low, i.e., 3 mm to 10 mm, and a noise is large.

SUMMARY OF THE INVENTION

It is an object of the present invention to provide a low-cost diagnosis apparatus which uses an XCT and a normal contrast medium, and achieves a high resolution.

According to the present invention, there is provided a diagnosis apparatus using an XCT, comprising an X-ray scanner for dynamically scanning a subject using an X-ray, an injector for injecting a contrast medium into the subject, a data collector for collecting data obtained by the X-ray scanner, an image reconstruction device for reconstructing an image in accordance with the collected data to generate image data corresponding to a plurality of tomograms including an angiogram, and an image analyzing device for analyzing the image data obtained by the image reconstruction device to calculate parameters each representing a state in which the contrast medium permeates blood vessels.

The injector injects an iodine-based contrast medium into the subject, and the X-ray scanner dynamically scans the subject. The image analyzing device calculates parameters at points in the tomograms to form functional images on the basis of these parameters.

BRIEF DESCRIPTION OF THE DRAWINGS

FIGS. 5 and 6 are graphs showing curves representing concentrations of a contrast medium which are obtained in various states of blood vessels;

DETAILED DESCRIPTION OF THE PREFERRED EMBODIMENTS

Figure 1:
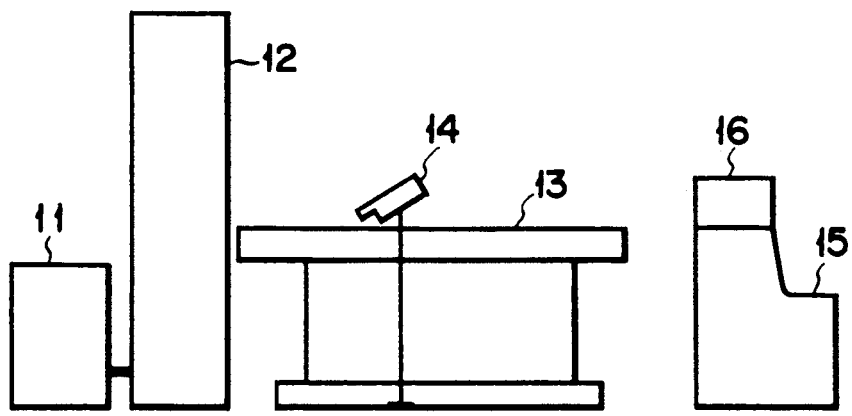
FIG. 1 is a schematic view showing a structure of a diagnosis apparatus using an XCT according to an embodiment of the present invention.

FIG. 1 shows an XCT (X-ray computed tomographic apparatus). This XCT includes a gantry 12 including an X-ray scanner for X-ray scanning a subject, an X-ray power source 11 for supplying power to the gantry 12, a couch 13, an injector 14 for injecting a contrast medium into the subject, a console 15, and a monitor 16.

Figure 2:
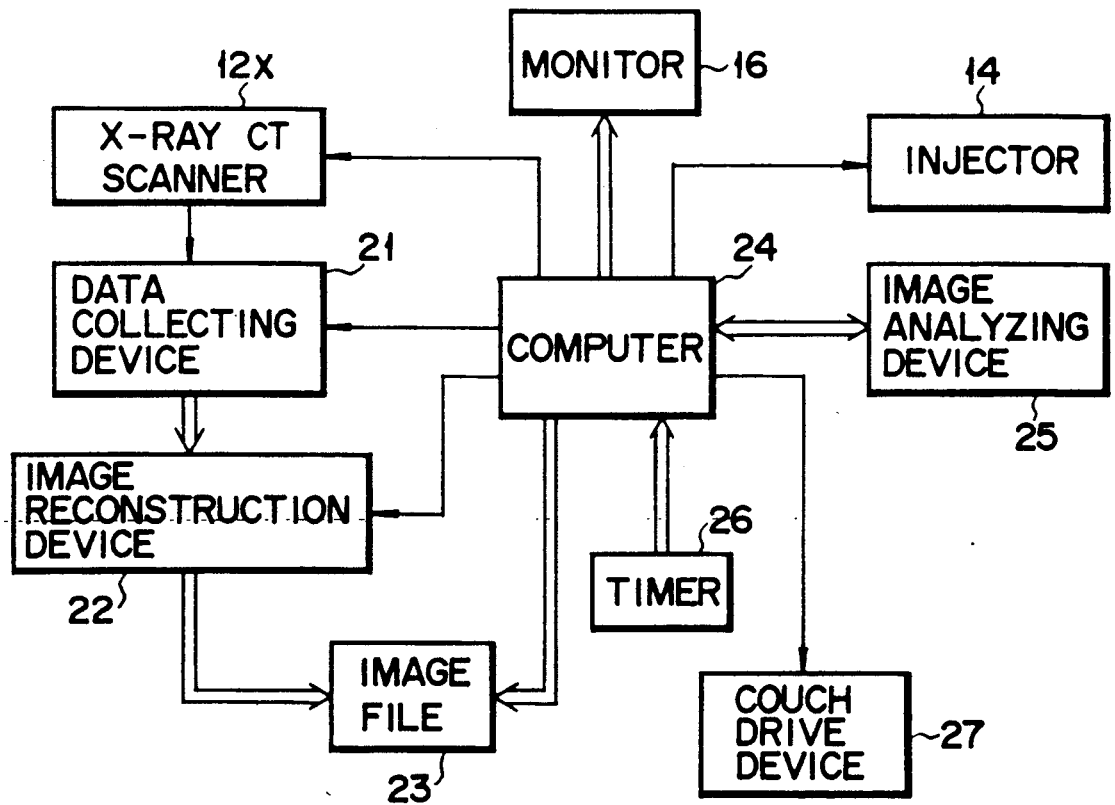
FIG. 2 is a block diagram of the diagnosis apparatus shown in FIG. 1.

FIG. 2 is a block diagram of the XCT. An output from an X-ray scanner 12x included in the gantry 12 is supplied to a data collecting device 21. The data collecting device 21 collects X-ray data obtained by the X-ray scanner. An output from the data collecting device 21 is supplied to an image reconstruction device 22. The image reconstruction device 22 processes the collected data to generate tomographic data. An output from the image reconstruction device 22 is supplied to an image file 23, and the tomographic data is stored in the image file 23.

The image file 23 is coupled to a computer 24, and image data is transferred through the computer 24. The computer 24 has a function for controlling the entire XCT, and is coupled to the X-ray scanner 12x, the data collecting device 21, the image reconstruction device 22, the injector 14, the monitor 16, an image analyzing device 25, a couch drive device 27, and a timer 26.

The image analyzing device 25 calculates parameters associated with points in the images in accordance with the image data, output from the image reconstruction device 22 and stored in the image file 23 to form functional image data.

An operation of the above-mentioned apparatus will be described hereinafter.

The subject (a head of a patient) is inserted in the gantry 12, and is fixed. Then, the X-ray scanner 12x is operated, and a single portion of the subject is scanned (dynamically scanned) by X-rays a plurality of times. Therefore, X-ray data corresponding to the subject is output from the X-ray scanner 12x, and is supplied to the data collecting device 21. At the same time as a scanning operation is started, or after the scanning operation is started, an iodine-based contrast medium is injected into the subject by the injector 14. After the contrast medium is injected, the X-ray scanner 12x intermittently and repeatedly scans the subject for about 30 minutes to output X-ray projection data. A time when the scanning operation is performed is counted by the timer 26.

Figure 3:
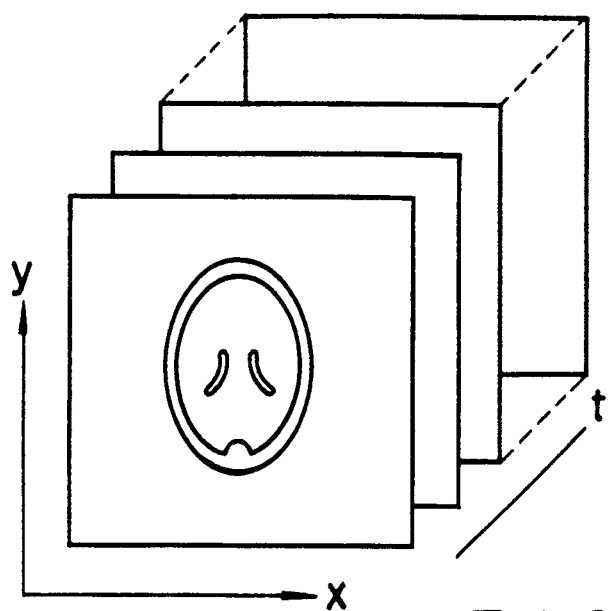
FIG. 3 is a view showing tomograms obtained by an X-ray scanning operation.

The data collecting device 21 collects the X-ray projection data from the X-ray scanner 12x to supply the collected data to the image reconstruction device 22. The collected data are converted into reconstructed image data by the reconstruction device The reconstructed image data is stored in the image file 23. In this case, as shown in FIG. 3, a plurality of reconstructed images along a time base (t) are stored in the image file 23 together with a time when the scanning operation is performed.

The images (FIG. 3) stored in the image file 23 are read out, and are input to the computer 24. At this time, as shown in a flow chart in FIG. 4, pixels P are smoothed in order to eliminate a noise component. Thereafter, CT value data at a position (x, y) of each pixel is collected along the time base t. In other words, data $Ci(t) = P(x, y, t)$ are collected as changes in CT value. By collecting data $Ci(t)$, e.g., three types of curves B, C, and D, in FIGS. 5 and 6, each representing a concentration of a contrast medium in blood can be obtained for three different pixels. Note that a curve A represents a concentration ($Cp(t)$) of a contrast medium in blood vessels measured using a given method (to be described later), the curve B represents a concentration of a contrast medium in a tissue having many blood vessels, and the curve C represents a concentration of a contrast medium in a normal tissue. The curve D in FIG. 6 represents a concentration of a contrast medium in a tissue in which the contrast medium leaks.

The image analyzing device 25 determines parameters Kb, λ, V, and p by a method of least squares using the data $Ci(t)$ and the concentration $Cp(t)$, as follows:

$$Ci(t) = \lambda Kb \left(1 - \frac{Vp}{1 - b \cdot Htc}\right) \int_0^t Cp(s)e^{(s-t)kb}ds + VpCp(t) \quad (1)$$

where $Cp(t)$ is the concentration of a contrast medium in blood vessels which is measured in advance, Kb is the rate of a leak, λ is the amount of gaps in a tissue, Vp is the amount of blood vessels, Htc is a hemafocrit value in a broad blood vessel, i.e., an amount of solid components in the blood, and b is a ratio of a hemafocrit value of a peripheral vessel to that of a broad blood vessel.

The concentration $Cp(t)$ can be obtained by either one of the following methods.

(1) A change in CT value of a broad blood vessel such as a sinus venosus in a head is measured based on the images stored in the image file.

(2) A change in average of the CT values in a normal tissue in the head is detected. Since the contrast medium causes almost no leak in a normal tissue, a concentration of the contrast medium in a normal tissue is in proportion to a concentration of that in blood vessels. Therefore, the concentration in a normal tissue can be used as the concentration in blood vessels. In this case, the concentration is defined as $V \cdot Cp(t)$, where V is the ratio of a volume of the blood vessels in the normal tissue. When the above calculation is performed, the parameters λ and Kb which are obtained by the method of least squares are not changed, but the parameter Vp is slightly changed. Therefore, a value which is defined as a standard value in anatomy is used as the ratio V. In this case, the value Vp has an error corresponding to only an error of the ratio V. If the ratio V is C times an actual value V, i.e., C·V, the value Vp is C times an actual value Vp.

In contrast to this, if V = 1, Vp = Vp/V. More specifically, Vp is not a volume ratio of the blood vessels in the normal tissue, but is a coefficient representing a ratio of the amount of blood vessels as compared with the amount V of blood vessels in a normal tissue. Although this coefficient Cp is less valuable than the volume ratio of blood vessels, it is effective data to perform diagnosis.

(3) Blood is repeatedly sampled and is analyzed by a bio-chemical analysis to measure a concentration of a contrast medium.

(4) The blood vessels simultaneously scanned to obtain CT values in blood in the blood vessels in the arm.

(5) A shunt tube through which blood flows is connected to the subject, and is scanned together with the head, thus obtaining data $Ct(t)$ in accordance with the CT values in the blood in the shunt tube.

Figure 4:
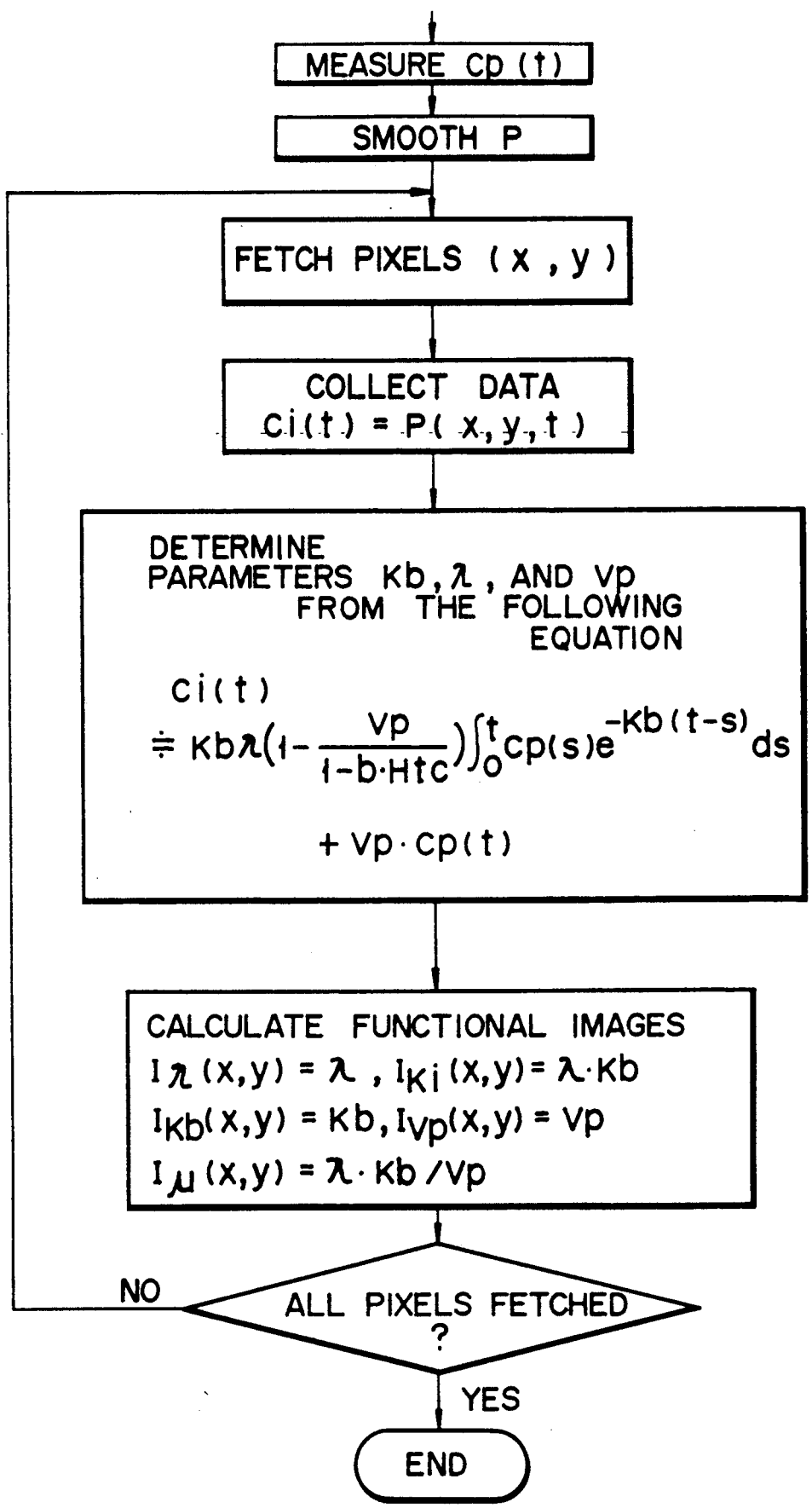
FIG. 4 is a flow chart for explaining an operation of the diagnosis apparatus of the present invention.

Image analysis based on the flow chart in FIG. 4 is repeatedly performed with respect to all pixels. Parameters Kb, λ, and Vp of all the pixels are obtained by the image analyzing device 25 to form functional images. In addition, when these parameters are combined, other functional images can be formed. Some arrangements of the functional images which are effective to perform diagnosis are as follows.

$I\lambda(x, y) = \lambda$ $IKi(x, y) = \lambda \times Kb$ $IKb(x, y) = Kb$ $IVp(x, y) = \lambda \times Vp$ $IPe(x, y) = \lambda \times Kb/Vp$ In the above factors of the functional images, Iλ is a gap in a cell tissue. When λ=1, all the tissue is a gap, and when λ=0, the tissue has no gaps. IKi represents permeability of the blood vessels; Kb, a rate of a leak (a reciprocal of a time constant); and IVp, an amount of blood vessels, i.e., an amount of blood vessels in a brain tissue having a predetermined volume. Iμ is a degree of a leak of a contrast medium per unit volume.

Figure 7A:
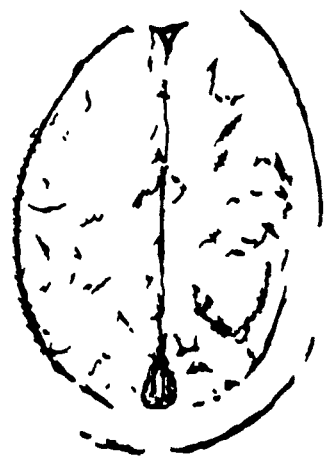
FIGS. 7A to 7D are views showing functional images.
Figure 7B:
Figure 7C:
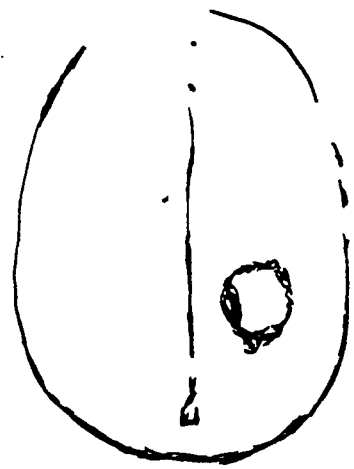
Figure 7D:

The functional images are monitored by the monitor 16 through the computer 24, and are stored in the image file 23. The functional images thus obtained are shown in FIGS. 7A to 7D. FIG. 7A is an image showing IVp, i.e., an amount of blood vessels, more specifically, an amount of blood vessels with respect to a brain tissue having a predetermined volume. A distribution of blood vessels (represented by black portions) in a head can be shown in this image. FIG. 7B is an image showing Kb, i.e., a rate of a leak. From this image, a rate of a breakage of the blood brain barrier, and a leak of a contrast medium into the brain cell tissue can be recognized. FIG. 7C is an image showing IKi, i.e., the permeability of blood vessels. From this image, a degree of permeability of blood vessels can be understood. FIG. 7D is an image showing Iλ, i.e., gaps in the cell tissue. From this image, a ratio of the gaps in the brain cell tissue can be understood. From these images, a state of the head, e.g., a crack in the blood vessels of the head, and an abnormality of the brain cell tissue can be diagnosed.

As described above, according to the present invention, a normal iodine-based contrast medium which does not pass through a blood brain barrier is used as a contrast medium, and the subject is scanned by an XCT.

A state of the blood vessels in the brain can be easily known in accordance with image data obtained by this CT scanning operation.

In the above-mentioned operation, the following method can be employed to obtain parameters.

A modification of the equation (1) yields equation (2):

$$Ci(t) = x_2 \int_0^t Cp(s)e^{-skb}ds + x_3 Cp(t) \tag{2}$$

where $$x_1 = Kb \tag{3}$$

$$x_2 = Ki\left(1 - \frac{Vp}{1 - b \cdot Htc}\right)e^{-tkb}$$

$$x_3 = Vp$$

If the values $x_1$ to $x_3$ can be determined, parameters Kb, Ki, and Vp can be obtained because the values b and Htc are known. Equation (2) can be rewritten as the following equation (2'):

$$Ci(t) = (x_2 + x_1 x_2) \int_0^t Cp(s)ds - x_1 \int_0^t Ci(s)ds + xCp(t) \tag{2'}$$

Equaiton (2') can be rewritten as follows:

$$Ci(t) = Z_1 F_1(t) + Z_2 F_2(t) + Z_3 F_3(t) \tag{2''}$$

where:

$$Z_1 = x_2 + x_1 x_3 \tag{4}$$

$$Z_2 = -x_1$$

$$Z_3 = x_3$$

$$F_1(t) = \int_0^t Cp(s)ds \tag{4'}$$

$$F_2(t) = \int_0^t Ci(s)ds$$

$$F_3(t) = Cp(t)$$

$F_2(t)$ includes an unknown function Ci. However, it is an object in this case to obtain Ci(t) which coincides with Y(t). Therefore, Ci can be assumed to be substantially approximate to data y. For this reason, equation (5) can be obtained.

$$Ci(t) \approx y(t) \tag{5}$$

Therefore, equation (6) can be obtained.

$$F_2(t) \approx \int_0^t y(s)ds \tag{6}$$

If $$F_2'(t) = \int_0^t y(s)ds$$

is used instead of $F_2(t)$, the following equation (7) can be obtained.

$$Ci(t) \approx Z_1 F_1(t) + Z_2 F_2'(t) + Z_3 F_3(t) \tag{7}$$

Thus, Ci(t) can be approximate to a linear coupling of known functions $F_1$, $F_2$, and $F_3$. The parameters $Z_1$, $Z_2$, and $Z_3$ are determined so that the function Ci(t) is most approximate to the function y(t) at points $t = t_1, t_2, \ldots, t_n$. Since equation (7) is a linear equation, a linear method of least squares can be used in order to determine parameters $Z_1$, $Z_2$, and $Z_3$. A residual sum of squares E can be defined as follows:

$$E = \sum_{j=1}^{n} (Ci(tj) - y(tj))^2 \tag{8}$$

In order to obtain $Z_1$, $Z_2$, and $Z_3$ for minimizing the sum E, the following equation (9) may be solved:

$$\frac{\partial E}{\partial Z_1} = \frac{\partial E}{\partial Z_2} = \frac{\partial E}{\partial Z_3} = 0 \tag{9}$$

When partial differentials of the equations (7) and (8) are obtained in practice, the following simultaneous equations with three unknowns can be obtained:

$$\sum_{j=1}^{N} F_1(tj)(Z_1 F_1(tj) + Z_2 F_2(tj) + Z_3 F_3(tj)) = \Sigma F_1(tj)y(tj) \tag{10}$$

$$\sum_{j=1}^{N} F_2(tj)(Z_1 F_1(tj) + Z_2 F_2(tj) + Z_3 F_3(tj)) = \Sigma F_2(tj)y(tj)$$

$$\sum_{j=1}^{N} F_3(tj)(Z_1 F_1(tj) + Z_2 F_2(tj) + Z_3 F_3(tj)) = \Sigma F_3(tj)y(tj)$$

When the above equations are solved, the parameters $Z_1, Z_2$, and $Z_3$ which minimize the sum E in equation (8) can be obtained. In other words, Ci(t) which is most approximate to y(t) can be determined. More specifically, when the values $x_1$, $x_2$, and $x_3$ are calculated on the basis of the obtained parameters $Z_1$, $Z_2$, and $Z_3$ using the relationship in equation (4), and the resultant values are substituted in equation (2), the approximate valve of Ci(t) can be calculated for an arbitrary value t.

Since the values $x_1$, $x_2$, and $x_3$ are calculated, the parameters Kb, Ki, and Vp can be obtained using the equation (3). In addition, $\lambda = Ki/Kb$, and $Pe = Ki/Vp$ can be calculated. Note that the values $\lambda$ and Pe are secondarily calculated on the basis of the parameters Kb, Ki, and Vp.

As is apparent from the above calculation, unknown functions are nonlinearly combined in equation (1). When Ci(t) is defined to match with y(t) in accordance with equation (1), a non-linear method of least squares must be used. Therefore, a calculation amount is undesirably increased. On the contrary, by using approximate values as in equations (6) and (7), these values are fed back to the linear method of least squares, thus achieving a remarkably easy calculation.

Figure 8A:
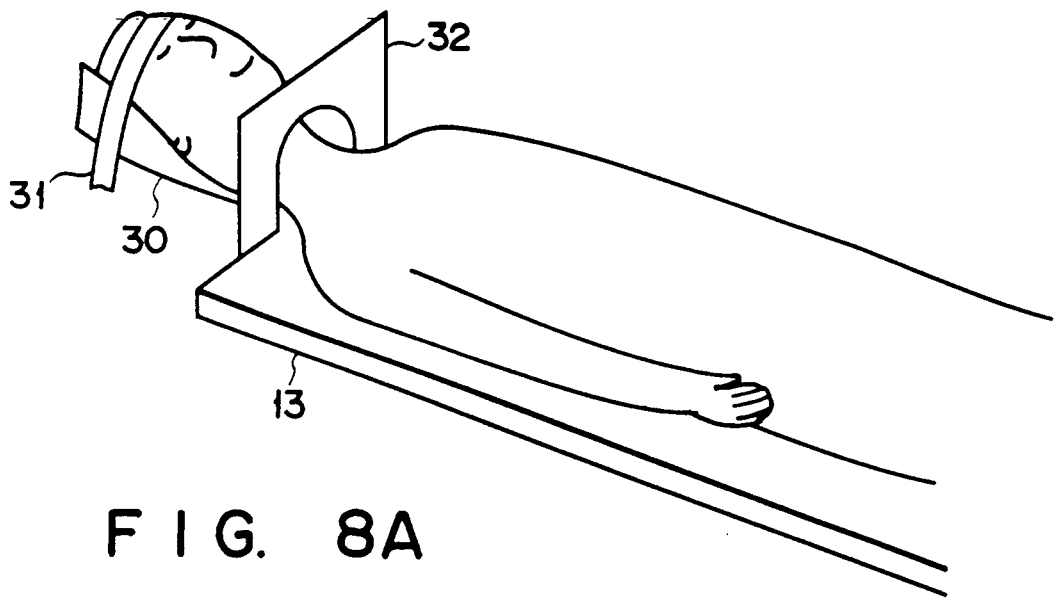
FIGS. 8A and 8B are views showing a state in which a patient is fixed in position.
Figure 8B:
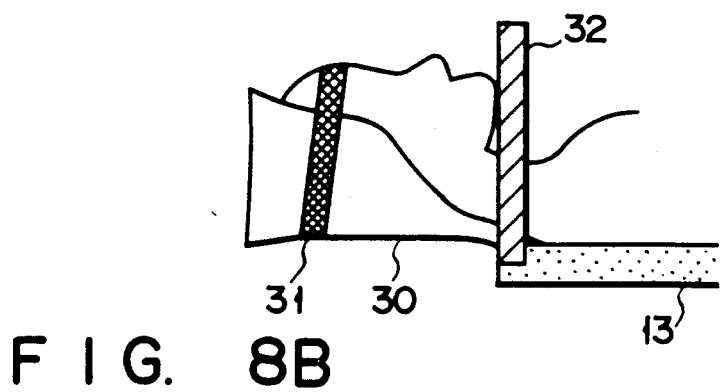

In order to obtain accurate data of BBB using the diagnosis apparatus according to the present invention, in an X-ray scanning operation, a portion of a patient must be fixed in position so that the patient does not move. As shown in FIG. 8, therefore, a head rest 30 is fixed to the couch 13. The head of the patient is placed on the head rest 30, and is reliably fixed to the head rest 30 with a band 31. In addition, a chin holding plate 32 is mounted to the couch 13 to fix the chin of the patient. The head can be fixed by the head rest 30 and the chin holding plate 32. However, if the patient moves, an accurate distribution of a concentration of a contrast medium cannot be obtained because an image obtained when t = 0 is subtracted from an image at tj to obtain the distribution of the concentration of the contrast medium. Therefore, the patient is reliably fixed with, e.g., the band.

Even if the patient moves due to, e.g., a looseness of the band although the patient is fixed to the couch as described above, a moving amount of the patient is detected, and the position of the image can be corrected in image processing.

Although one slice region is scanned several times to obtain a plurality of functional images in the above embodiment, a plurality of slice regions may be simultaneously scanned to obtain a plurality of functional images of the slice regions.

A series of functional images thus obtained which are associated with the plurality of slices may be three-dimensionally processed to monitor a distribution of the blood vessels or the like by three-dimensional images.

In addition, a multi-slice operation can be performed, i.e., a predetermined portion is sliced into a plurality of portions at predetermined intervals, and the integral of the parameters in the predetermined portion can be measured based on a plurality of functional images obtained. More specifically, values of all pixels included in a region of interest are integrated for all the images. An integral V is obtained as follows:

$$V = \sum_{i=1}^{K} Si \times \Delta h \times \Delta P^2 \quad (11)$$

where Si is the sum, k is the number of slices, $\Delta h$ is the interval of the slices (mm), and $\Delta P$ is the pixel size (mm).

For example, if the above equation is applied to the functional image IVp, the volume of blood vessels in a tumor can be measured. When the above equation is applied to the functional image Iλ, and the following equation is used, an average of a ratio of gaps of a cell in the tumor can be obtained:

$$R = \frac{V}{\sum_{j=1}^{K} \Delta h \Delta P^2} \quad (12)$$

In gamma fitting conventionally used to analyze a CT image, a time period until blood flows out a tissue after it flows into the tissue, i.e., an average passing time period, can be obtained. When an average passing time period Tm of blood measured by gamma fitting is combined with Vp measured in the present invention, a local average flowing amount of blood can be obtained based on Vp/Tm.

Note that although a state of BBB in a brain is measured in the above embodiment, the present invention can be used to measure a state of other portions such as a liver.

According to the present invention, a normal contrast medium such as an iodine-based contrast medium, and CT scanning is performed by the XCT. Therefore, a high-resolution diagnosis image can be obtained, and a safe and low-cost apparatus for diagnosing a state of permeability of blood vessels can be provided.

What is claimed is:

1. A diagnostic apparatus using an X-ray CT device, comprising:

X-ray scanning means for repeatedly scanning one or more portions of a subject using an X-ray a plurality of times for each portion to output X-ray projection data;

image processing means for processing the X-ray projection data output from said scanning means to generate image data corresponding to a plurality of tomograms with contrast; and image analyzing means for analyzing the image data obtained by said image processing means to calculate a set of parameters which represents a state of permeability of blood vessels, by collecting CT value data of an identical location for a time t from the series of image data, and generating concentration data representing concentrations of contrast medium in the blood vessels, and calculating the parameters in accordance with the CT value data and the concentration data.

2. An apparatus according to claim 1, wherein said image analyzing means comprises means for calculating an amount of a contrast medium which leaks from the blood vessels, an amount of the blood vessels, and gaps between cells in accordance with the image data.

3. An apparatus according to claim 1, further comprising an injector for injecting an iodine-based contrast medium into a subject, the subject including the blood vessels.

4. An apparatus according to claim 1, wherein said image processing means comprises data collecting means for collecting the X-ray projection data to output the collected data, and reconstructing means for converting the collected data into reconstructed image data.

5. An apparatus according to claim 1, wherein said image analyzing means comprises means for combining the parameters to form functional images.

* * * * *